United States Patent
Keays et al.

(10) Patent No.: US 9,922,508 B2
(45) Date of Patent: Mar. 20, 2018

(54) BIORESISTIVE-FINGERPRINT BASED SOBRIETY MONITORING SYSTEM

(71) Applicant: SOBERLINK HEALTHCARE, LLC, Huntingdon Beach, CA (US)

(72) Inventors: Brad Keays, Manhattan Beach, CA (US); Christopher J. Pursley, Fullerton, CA (US); Daniel Rhodes, San Diego, CA (US); Casey Hanrahan, Fullerton, CA (US)

(73) Assignee: SOBERLINK HEALTHCARE, LLC, Huntington Beach, CA (US)

( * ) Notice: Subject to any disclaimer, the term of this patent is extended or adjusted under 35 U.S.C. 154(b) by 0 days.

(21) Appl. No.: 15/289,881

(22) Filed: Oct. 10, 2016

(65) Prior Publication Data

US 2017/0132883 A1 May 11, 2017

Related U.S. Application Data

(60) Provisional application No. 62/239,648, filed on Oct. 9, 2015.

(51) Int. Cl.
| | |
|---|---|
| *G08B 1/08* | (2006.01) |
| *H04B 1/3827* | (2015.01) |
| *G01N 33/497* | (2006.01) |
| *G06K 9/00* | (2006.01) |

(52) U.S. Cl.
CPC ........... *G08B 1/08* (2013.01); *G01N 33/4972* (2013.01); *H04B 1/3833* (2013.01); *G06K 9/00087* (2013.01)

(58) Field of Classification Search
CPC .... G08B 1/08; G01N 33/4972; H04B 1/3833; G06K 9/00087
See application file for complete search history.

(56) References Cited

U.S. PATENT DOCUMENTS

| | | |
|---|---|---|
| 3,437,449 A | 4/1969 | Luckey |
| 4,093,945 A | 6/1978 | Collier et al. |
| 4,132,109 A | 1/1979 | VanderSyde |
| 4,564,021 A | 1/1986 | Siegmann et al. |
| 4,843,377 A | 6/1989 | Fuller et al. |
| 5,220,919 A | 6/1993 | Phillips et al. |
| 6,026,674 A | 2/2000 | Gammenthaler |
| 6,726,636 B2 | 4/2004 | Der Ghazarian et al. |
| 6,748,792 B1 | 6/2004 | Freund et al. |
| 6,837,095 B2 | 1/2005 | Sunshine et al. |
| 6,899,683 B2 | 5/2005 | Mault et al. |
| 7,341,693 B2 | 3/2008 | Der Ghazarian et al. |
| 7,462,149 B2 | 12/2008 | Hawthorne et al. |
| 7,611,461 B2 | 11/2009 | Hawthorne et al. |
| 7,636,047 B1 | 12/2009 | Sempek |
| 7,641,611 B2 | 1/2010 | Hawthorne et al. |
| 7,833,166 B2 | 11/2010 | Ruffert |

(Continued)

FOREIGN PATENT DOCUMENTS

WO WO 2008/076310 A1 6/2008

OTHER PUBLICATIONS

WO, PCT/US2010/050930 ISR, dated Dec. 2, 2010.

(Continued)

*Primary Examiner* — Erin File
(74) *Attorney, Agent, or Firm* — One LLP; Joseph K. Liu

(57) ABSTRACT

A system and method of monitoring sobriety using a hand-held breath testing device that, on receipt of a user's breath, generates a breath test signal comprising substance content data and user identification data, and wirelessly transmits the breath test signal to a breath test signal receiving station, and wherein the breath testing device further includes a fingerprint reader and a plurality of sensors.

19 Claims, 4 Drawing Sheets

(56) References Cited

U.S. PATENT DOCUMENTS

| | | | |
|---|---|---|---|
| 7,841,224 B2 | 11/2010 | Son | |
| 7,934,577 B2 | 5/2011 | Walter et al. | |
| 8,249,311 B2 | 8/2012 | Endo et al. | |
| 8,280,436 B2 | 10/2012 | Harris, Jr. | |
| 8,381,573 B2 | 2/2013 | Keays | |
| 8,707,758 B2 | 4/2014 | Keays | |
| 9,228,997 B2 | 1/2016 | Keays | |
| 2002/0084130 A1 | 7/2002 | Der Ghazarian et al. | |
| 2002/0127145 A1 | 9/2002 | Der Ghazarian et al. | |
| 2002/0177232 A1 | 11/2002 | Melker et al. | |
| 2003/0004403 A1 | 1/2003 | Drinan et al. | |
| 2003/0117287 A1* | 6/2003 | Crespo | A61B 5/18 340/576 |
| 2004/0236199 A1 | 11/2004 | Hawthorne et al. | |
| 2004/0239510 A1 | 12/2004 | Karsten | |
| 2005/0065446 A1 | 3/2005 | Talton | |
| 2006/0009257 A1 | 1/2006 | Ku | |
| 2006/0202838 A1 | 9/2006 | Hawthorne et al. | |
| 2007/0016092 A1 | 1/2007 | Shaw et al. | |
| 2007/0062255 A1 | 3/2007 | Talton | |
| 2007/0144812 A1 | 6/2007 | Stewart et al. | |
| 2007/0239992 A1 | 10/2007 | White et al. | |
| 2007/0258894 A1 | 11/2007 | Melker et al. | |
| 2007/0261468 A1 | 11/2007 | Crespo et al. | |
| 2008/0009693 A1 | 1/2008 | Hawthorne et al. | |
| 2008/0183502 A1 | 7/2008 | Dicks et al. | |
| 2008/0314115 A1 | 12/2008 | Faulder et al. | |
| 2009/0053110 A1 | 2/2009 | Chanq et al. | |
| 2009/0060287 A1 | 3/2009 | Hyde et al. | |
| 2009/0182216 A1 | 7/2009 | Roushev, III et al. | |
| 2009/0201138 A1 | 8/2009 | Ghazarian et al. | |
| 2009/0247892 A1* | 10/2009 | Castrodale | A61B 5/097 600/543 |
| 2009/0293589 A1 | 12/2009 | Freund et al. | |
| 2010/0012417 A1 | 1/2010 | Walter et al. | |
| 2010/0028210 A1* | 2/2010 | Ozaki | B60K 28/063 422/84 |
| 2010/0089121 A1 | 4/2010 | Hemminqsson et al. | |
| 2010/0138166 A1 | 6/2010 | Do et al. | |
| 2010/0204600 A1 | 8/2010 | Crucilla | |
| 2010/0251804 A1 | 10/2010 | Morley et al. | |
| 2011/0304465 A1* | 12/2011 | Boult | B60K 28/06 340/576 |
| 2012/0022890 A1* | 1/2012 | Williams | G06Q 50/22 705/3 |
| 2012/0031166 A1 | 2/2012 | Lopez et al. | |
| 2012/0075094 A1 | 3/2012 | Keays | |
| 2012/0242469 A1 | 9/2012 | Morgan et al. | |
| 2012/0302907 A1 | 11/2012 | Palmskog et al. | |
| 2013/0006068 A1 | 1/2013 | Gemer et al. | |
| 2013/0021153 A1 | 1/2013 | Keays | |
| 2013/0200907 A1* | 8/2013 | Schneider | G06K 9/0002 324/686 |
| 2013/0282321 A1* | 10/2013 | Son | G01N 33/4972 702/104 |
| 2014/0003676 A1* | 1/2014 | Baughman | G06K 9/00006 382/124 |
| 2014/0041436 A1 | 2/2014 | Knott et al. | |
| 2014/0062722 A1* | 3/2014 | Ofir | G01N 27/26 340/870.02 |
| 2014/0311215 A1* | 10/2014 | Keays | G01N 33/497 73/23.3 |
| 2015/0084774 A1 | 3/2015 | Wojcik et al. | |
| 2017/0035332 A1* | 2/2017 | Wahnschafft | A61B 5/14546 |
| 2017/0146502 A1* | 5/2017 | Son | G01N 33/4972 |

OTHER PUBLICATIONS

WO, PCT/US2010/050930 IPRP, dated Apr. 3, 2012.
WO, PCT/US2014/029411 ISR, dated Jul. 28, 2014.
WO, PCT/US2014/029411 IPRP, dated Sep. 15, 2015.
CA, 2,780,108 Office Action, dated Mar. 31, 2015.
WO, PCT/US2015/064570 ISR and Written Opinion, dated Feb. 11, 2016.
Ahlber, P. "Electronic Nose Offers Food Processors a Powerful New Smell Identification Tool," Food Online. Mar. 13, 2000. Accessed online <http://www.foodonline.com> on Jul. 29, 2013.
Angell, L.C., "iBreath iPod add-on features alcohol breathalyzer," <http://www.ilounge.com>, published online Sep. 11, 2006.
Berchtold, C., et al., "Evaluation of extractive electrospray ionization and atmospheric pressure chemical ionization for the detection of narcotics in breath", International Journal of Mass Spectrometry, 2011, vol. 299, pp. 145-150.
CNET Reviews, "iBreath: the iPhone Breathalyzer," <http://reviews.cnet.com>, published online on Dec. 15, 2008.
Fariva, C., "iBreath, your iPod-powered breathalyzer," <http://www.engadget.com>, published online on Sep. 12, 2006.
"Hand-held Analytical Power for Workplace Monitoring," News Release from Quantitech Ltd, Jul. 2, 2004. Accessed on line on Jul. 29, 2013 at <http://www.edie.net/news/O/Hand-held-Analytical-Power-for-Workplace-Monitoring/8540/>.
Manolis, A., "The Diagnostic Potential of Breath Analysis," Clin. Chem. 29/1, pp. 5-15 (1983).
Millward, D., "Motorists face roadside drug tests under government plans," Telegraph. May 10, 2009.
Millward, D., "Roadside drug testing device developed by academics," Telegraph. Nov. 15, 2011.
Mullett, G., Wireless Telecommunications Systems and Networks (Thomson 2006).
"New technique enables drugs tests via exhaled breath", Karolinska Institutet, 2010, retrieved from < http://www.sciencedaily.com/releases/2010/05/100519081438.htm> on Jul. 22, 2015.
http://www.intoxalock.com/intoxalock-alcohol-monitoring-systems.cfm (printed at least as early as Oct. 15, 2012).
http://www.web.archive.org/web/20090311081549/http://alcoholmonitoring.com/index/scram/what-is-scram (printed at least as early as Oct. 15, 2012).
Electronic Monitoring System, MEMS 3000 Homestation Installation Guide, Elmo Tech LTD., Mar. 2006.
Intoxalock Overview: Mobile eLERT Camera, <http://intoxalock.com/mobile-elert-camera.cfm>, print date: Dec. 4, 2012.
IPR2013-00577 (Paper 5), Amended Petition for Inter Partes Review (dated Sep. 20, 2013).
IPR2013-00577 (Paper 10), Preliminary Response (dated Dec. 9, 2013).
IPR2013-00577 (Paper 12), Institution Decision (dated Feb. 13, 2014).
IPR2013-00577 (Paper 22), Patent Owner Response (dated May 7, 2014).
IPR2013-00577 (Paper 26), Petitioner Reply (dated Jul. 21, 2014).
IPR2013-00577 (Paper 40), Final Decision (dated Jan. 13, 2015).
IPR2013-00577 (Ex. 1019), Decl. of McAlexander III (dated Sep. 9, 2013).
IPR2013-00577 (Ex. 1020), Decl. of McAlexander III, continued (dated Sep. 9, 2013).
IPR2015-00556 (Paper 2), Petition for Inter Partes Review (dated Jan. 12, 2015).
IPR2015-00556 (Paper 7), Decision Institution of Inter Partes Review (dated Jul. 16, 2015).
IPR2015-00556 (Ex. 1104), "MEMS 3000 Homestation Installation Guide," ElmoTech, Ltd. (Mar. 2006).
IPR2015-00556 (Ex. 1107), Borkenstien & Smith, "The Breathalyzer and its Application," 2 Medicine, Science, and the Law 13 (1962).
IPR2015-00556 (Ex. 1116), Depo. Tr. of Dr. Skipper, (dated Jun. 25, 2014).
IPR2015-00556 (Ex. 1124), Decl. of Wojcik, (dated Jan. 12, 2015).
IPR2015-00556 (Ex. 1130), Paul Diggan, "Long Arm of the Law has Man by the Ankle," Washington Post (Mar. 18, 2005).
IPR2015-00556 (Ex. 1131), Wayback Machine Archive: www.bi.com/sobrietor (accessed: Nov. 15, 2014).
IPR2015-00556 (Ex. 1132), Mike Hanlon, "The LG Breathalyzer Phone," Gizmag (Jul. 7, 2006).
IPR2015-00556 (Ex. 1133), CNET Staff, "iBreath: the iPhone Breathalyzer," CNET (Dec. 14, 2008).

(56) References Cited

OTHER PUBLICATIONS

IPR2015-00556 (Ex. 1134), Wayback Machine Archive: www.sentalt.com/vicap.htm (accessed: Nov. 15, 2014).
IPR2015-00556 (Ex. 1135), "Program monitors alcohol-related offenders," Rapid City Journal (Feb. 29, 2004).
IPR2015-00556 (Ex. 1136), Wayback Machine Archive: www.isecuretrac.com/services.aspx?p=alcoholmonitoring (accessed: Nov. 15, 2014).
IPR2015-00556 (Ex. 1137), "MEMS 3000 Cellular Receiver and Transmitter Installation Guide," ElmoTech, Ltd. (submitted on Jan. 12, 2015).
IPR2015-00556 (Ex. 1138), Wayback Machine Archive: www.spartstartinc.com/index.php/products/in-house (accessed: Nov. 17, 2014).
IPR2015-00556 (Ex. 1139), Wayback Machine Archive: www.streetimetechnolgies.com/products/mobilebreath (accessed: Dec. 9, 2014).
IPR2015-00556 (Ex. 1141), Wayback Machine Archive: http://tsc.trackingsystemscorp.com/mem4.htm (accessed: Nov. 17, 2014).
IPR2015-00556 (Ex. 1142), "MEMS 3000 Homestation & Transmitter Installation Guide," ElmoTech, Ltd. (Sep. 2005).
IPR2015-00556 (Ex. 1143), Editorial Staff, "LifeSafer Interlock Launches the Portable and Home Alcohol Monitoring System," LifeSafer (Jun. 15, 2011).
IPR2015-00556 (Ex. 1144), Douglass Martin, "Robert F. Borkenstein, 89, Inventor of the Breathalyzer," New York Times (Aug. 17, 2002).
IPR2015-00556 (Ex. 1145), "iSECUREtrac In-home Alcohol Testing," iSECUREtrac (submitted on Jan. 12, 2015).
IPR2015-00556 (Ex. 1146), "Electronic Home Monitoring Services Offered by Alternative Corrections, Inc.," Alternative Corrections, Inc. (submitted on Jan. 12, 2015).
IPR2015-00556 (Ex. 1147), Wayback Machine Archive: www.alertinc.us/electronic_monitoring_equipment.htm (accessed: Nov. 24, 2014).
IPR2015-00556 (Ex. 1148), Wayback Machine Archive: www.questguard.com/Breathalyzer-Testing_.html (accessed: Nov. 11, 2014).
IPR2015-00556 (Ex. 1149), Dept. Transp., "Highway Safety Programs; Conforming Products List of Screening Devices to Measure Alcohol in Bodily Fluids," 59 Fed. Reg. 231 (Dec. 2, 1994).
IPR2015-00556 (Ex. 1150), Dept. Transp., "Highway Safety Programs; Conforming Products List of Screening Devices to Measure Alcohol in Bodily Fluids," 47 Fed. Reg. 239 (Dec. 15, 2009).
IPR2015-00556 (Ex. 1151), Globes Corresp., "Dmatek buys Mitsubishi's alcohol monitoring product line," Globes Israel's Business Arena (Sep. 12, 2002).
IPR2015-00556 (Ex. 1152), "BTI2 Electrical Specifications," Alcohol Countermeasure Systems (Sep. 29, 2004).
IPR2015-00556 (Ex. 1153), "MEMS 3000 GSM Operational Description," ElmoTech, Ltd. (submitted on Jan. 12, 2015).
IPR2015-00556 (Ex. 1154), "MEMS 3000 GSM Block Diagram," ElmoTech, Ltd. (submitted on Jan. 12, 2015).
Website: http://www.tokai-denshi.com/english/products/ALC-Mobile_1.html (accessed: Jul. 30, 2014).
Website: http://www.tokai-denshi.com/english/products/ALC-Mobile_3-1.html (accessed: Jul. 30, 2014).
Website: http://www.lifesafer.com/blog/lifesafer-interlock-launches-the-portable-and-home-alcohol-monitoring-system/ (accessed: Aug. 1, 2014).
Website: http://www.prnewswire.com/newsreleases/lifesafer-interlock-launches-the-portable-and-home-alcohol-monitoring-system-124662013.html (accessed: Aug. 1, 2014).
Website: http://www.smartstartinc.com/repository/nov2011-press-release/ (accessed: Aug. 1, 2014).
Website: http://www.eramonitoring.com/products_Mems3000.html (accessed: Aug. 1, 2014).
Website: http://web.archive.org/web/20081210155459/http://www.isecuretrac.com/services.aspx?p=alcoholmonitoring (accessed: Aug. 1, 2014).
Website: http://www.corrections.com/articles/11251-vi-cap-videoinformation-capture (accessed: Aug. 1, 2014).
Website: http://www.mobileinc.co.uk/2009/07/one-you-may-have-missed-the-lg-breathalyzer-phone/ (accessed: Aug. 1, 2014).
Website: http://www.smartstartinc.com/about-us/ (accessed: Aug. 1, 2014).
Website: http://www.smartstartinc.com/wpcontent/uploads/2014/04/Smart_Start_App_April_11_Final_Release.pdf (accessed: Aug. 1, 2014).
Website: http://www.webarchive.org/web/20110627002850/http://www.lifesafer.com/hmu.php (accessed: Aug. 1, 2014).
Website: http://www.webarchive.org/web/2011061122248/http://www.streetimetechnologies.com/products/mobilebreath (accessed: Aug. 1, 2014).
Website: http://bi.com/node/483 (accessed: Aug. 1, 2014).

\* cited by examiner

BIORESISTIVE-FINGERPRINT BASED SOBRIETY MONITORING SYSTEM

CROSS-REFERENCE TO RELATED APPLICATIONS

The present application claims benefit of priority with U.S. Provisional Application No. 62/239,648, filed Oct. 9, 2015, which is hereby incorporated by reference.

TECHNICAL FIELD

Embodiments of the present invention generally relate to remote sobriety monitoring, and more particularly to a method and system utilizing a breath testing and biometric identification device for periodically analyzing the alcohol content or other substance content of the breath of a user.

BACKGROUND OF THE INVENTION

One of the challenges in remotely monitoring someone's sobriety with a mobile breathalyzer is being able to say with certainty that the person being monitored was the same person taking a given breath test. Some current state of the art devices use a digital imager to take a photograph of the user as they blow into the device, and also rely on breath temperature and pressure sensors to determine if an air source other than the user's breath is being used. These devices were described in U.S. application Ser. No. 13/357, 494 (which is now U.S. Pat. No. 8,707,758, to Keays), U.S. application Ser. No. 13/274,553, and U.S. application Ser. No. 12/882,323 (which is now U.S. Pat. No. 8,381,573, to Keays), the entire contents and disclosures of which are herein incorporated by reference. This works well, however, the use of a digital imager presents several issues that are less than desirable. First, because the imager is typically close to the user's face when they blow into the device, a wide-angle lens is used to capture an image of the whole face. This results in an image with a "fish eye" effect, making user hard to recognize. Second, the digital image is sent with the test report. The smallest image that is practical to use is a 320×240 jpeg image. The maximum size of these images is roughly 20 Kbytes and is by far the largest piece of data contained in the breath test. The method outlined herein provides a means by which a user can be positively identified without the need for a digital image.

It would therefore be desirable to provide a method and system of providing supervisory monitoring of sobriety that is discrete, portable, tamper-proof, effective, and including bioresistive-fingerprint identification, and that can automatically alert a monitoring station of the need for attention and possible corrective or medical action by such a supervisory sober buddy or sober companion on an on-call basis. The present invention meets these and other needs.

SUMMARY OF THE INVENTION

Provided herein are embodiments of a handheld device for monitoring the sobriety of a user. The handheld device includes a mouth piece for receiving a user's mouth, a conductive area positioned on the mouthpiece, a user identification device positioned on a case of the handheld device, and a conductive area positioned on said user identification device.

In some embodiments, a handheld device is provided for monitoring the sobriety of a user. The handheld device includes a mouth piece for receiving a user's mouth and the user's breath, a conductive area positioned on said mouthpiece for receiving a first resistance measurement, a user identification device positioned on a case of the handheld device for receiving the user's fingerprint, a conductive area positioned on said user identification device for receiving a second resistance measurement, and a wireless transceiver.

These and other aspects and advantages of the invention will be apparent from the following detailed description and the accompanying drawing, which illustrates by way of example the features of the invention.

BRIEF DESCRIPTION OF THE DRAWINGS

Illustrated in the accompanying drawings is at least one of the best mode embodiments of the present invention In such drawings.

DETAILED DESCRIPTION OF THE INVENTION

Figure 1:
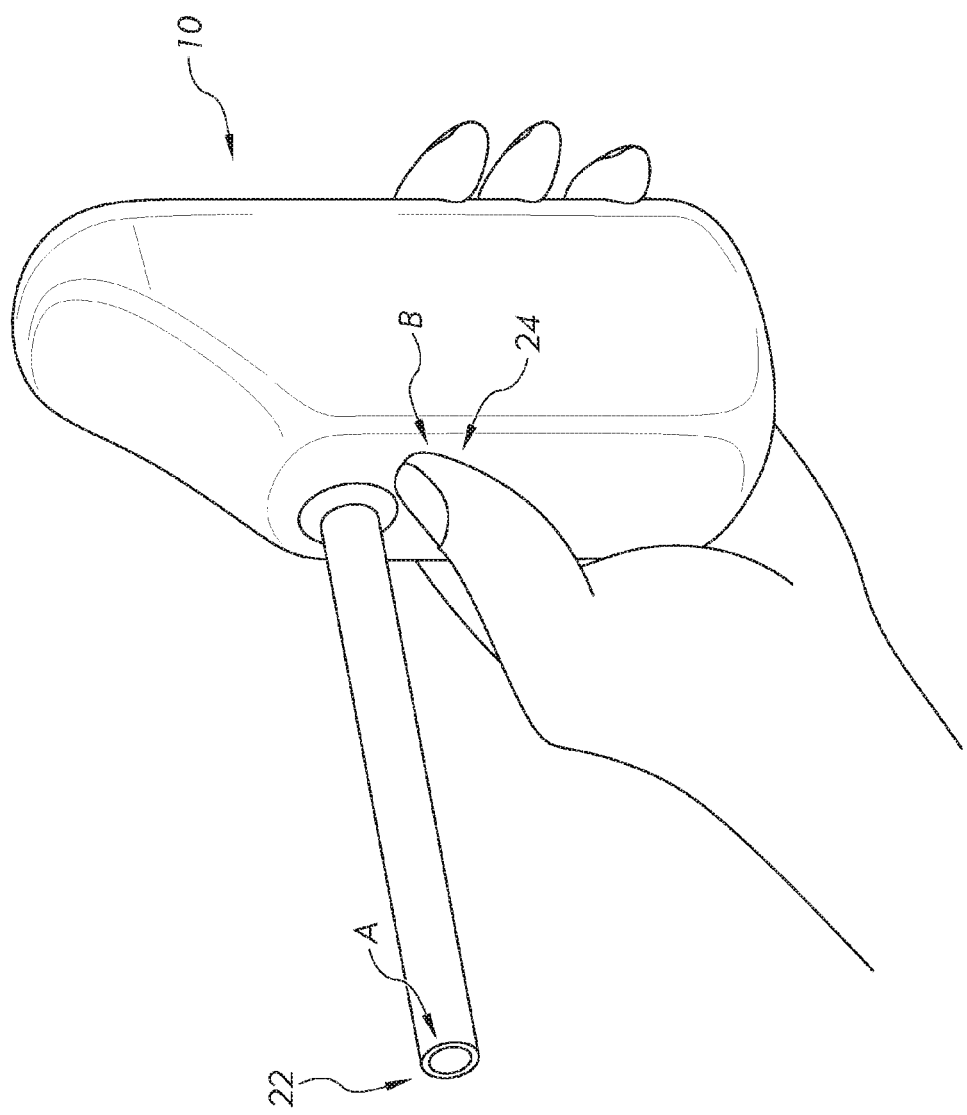
FIG. 1 is a perspective view illustrating a breath testing and identification device for monitoring sobriety, according to an embodiment of the invention.

The above described drawing figures illustrate the described apparatus and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

In the following description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B", when used in conjunction with open-ended language such as "comprising" can refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

Referring now to the drawings, wherein like reference numerals designate identical or corresponding parts throughout the several views and embodiments, FIGS. 1 to 4 illustrate embodiments of a system and method for sobriety monitoring, utilizing a breath testing and biometric identification device for analyzing the alcohol content or other substance content of the breath of a user in combination with a wireless or cellular transmitter or transceiver device to transmit an alcohol content or other substance content signal to a wireless or cellular signal receiver and/or monitoring station.

Briefly, and in general terms, the present invention provides for a method and system for monitoring sobriety of a user on an automated basis, utilizing a hand-held breath testing device, a wireless or cellular transmitter or transceiver device for wirelessly transmitting results of the breath testing to a wireless or cellular receiver monitoring station. The monitoring station receives the breath testing results (and optionally identification such as a fingerprint) from the wireless or cellular transmitter or transceiver device, and indicates an alarm or otherwise alerts an on-call monitor when the wireless or cellular transmitter or transceiver is indicated to be off, or when the breath testing results indicate a breath test content greater than a predetermined threshold, or when the received breath is not the breath of the user (which can be determined from the fingerprint and a resistance measurement as described herein in more detail). The method and system can be used in connection with a traditional sober buddy, chaperone service on an on-call basis only, to limit the expense and labor intensiveness of the supervisory care. Such a systems may also be used to monitor abstinence from other drugs which can be taken orally and tested by breath analyzer or the like without the use of a chaperone on a continuing basis.

A cellular module can alternatively be provided inside the breath testing and identification device that can send a breath test report directly through WiFi, cell towers, or through other mobile wireless networks such as those that do not rely on fixed infrastructure, for example.

Described now in detail is a method and system for monitoring sobriety of a user, for example, a recovering alcoholic, as an intermediate, automated way of engaging the services of a sober buddy, sober companion, sober coach, or other supervisory care for the user to help, for example, ensure against relapse of the user, and to help the user maintain sufficient abstinence from alcohol or another substance to reside and function outside of a treatment facility.

Fingerprint identification modules allow fingerprints to be used in lieu of a password in mobile devices such as phones, personal digital assistants (PDAs) and tablets. In order to use fingerprint identification, these devices train the module on what the users' fingerprints look like by having them place their finger on the module in several different orientations. Once trained, the module compares future fingerprints against these reference prints to determine if a known user is trying to access the device. However, using a fingerprint reader module alone in a breathalyzer is often not enough, for example, the user could simply use his own fingerprints but has someone else blow into the breathalyzer device. There needs to be a way to confirm that the person blowing into the device is the one whose fingerprints were used to initiate the test.

To solve this problem, generally, the system of the invention uses a "smart" mouthpiece for the user to blow into the device when taking a test. In some embodiments, the end of the device, where the user places his or her mouth during the blow, is conductive. A conductive element may also be placed at the fingerprint reader on the breathalyzer, so that when the user's finger is on the reader it comes in contact with the conductive element. After one or more fingerprints of the user have been used to positively identify the user, the device will take a resistance measurement between the fingerprint reader and the mouthpiece. If the resistance falls within a specified range, the device will determine that the finger currently on the fingerprint reader is "connected" to the mouth currently on the mouthpiece, and the fingerprint can be positively connected to the breath used for the test.

Referring now to FIG. 1, an exemplary embodiment of a substance testing device 10 is shown. In this embodiment, the substance testing device 10 is a breath testing device. The substance testing device 10 may include a mouthpiece 22 and a user identification device (UID) 24. The UID 24 is located on a wall of the case of the substance testing device 10. The UID 24 may be operable to generate a user identification data. In this example, the UID 24 is a fingerprint reader. In FIG. 1, area A is the conductive portion of the mouthpiece 22, area B is the conductive element of the UID 24. Area A is sized to ensure that the user's mouth will be in contact therewith while the user's mouth is placed on the mouthpiece 22. The UID 24 and area B will be in contact with, for example, a user's thumb (though any finger or multiple fingers may be used), while the user is operating (e.g., holding) the substance testing device 10. Although shown as a horizontally elongated tube, the mouthpiece 22 may be in other shape suitable for the user to place his or her mouth over and to breath into.

Figure 2:
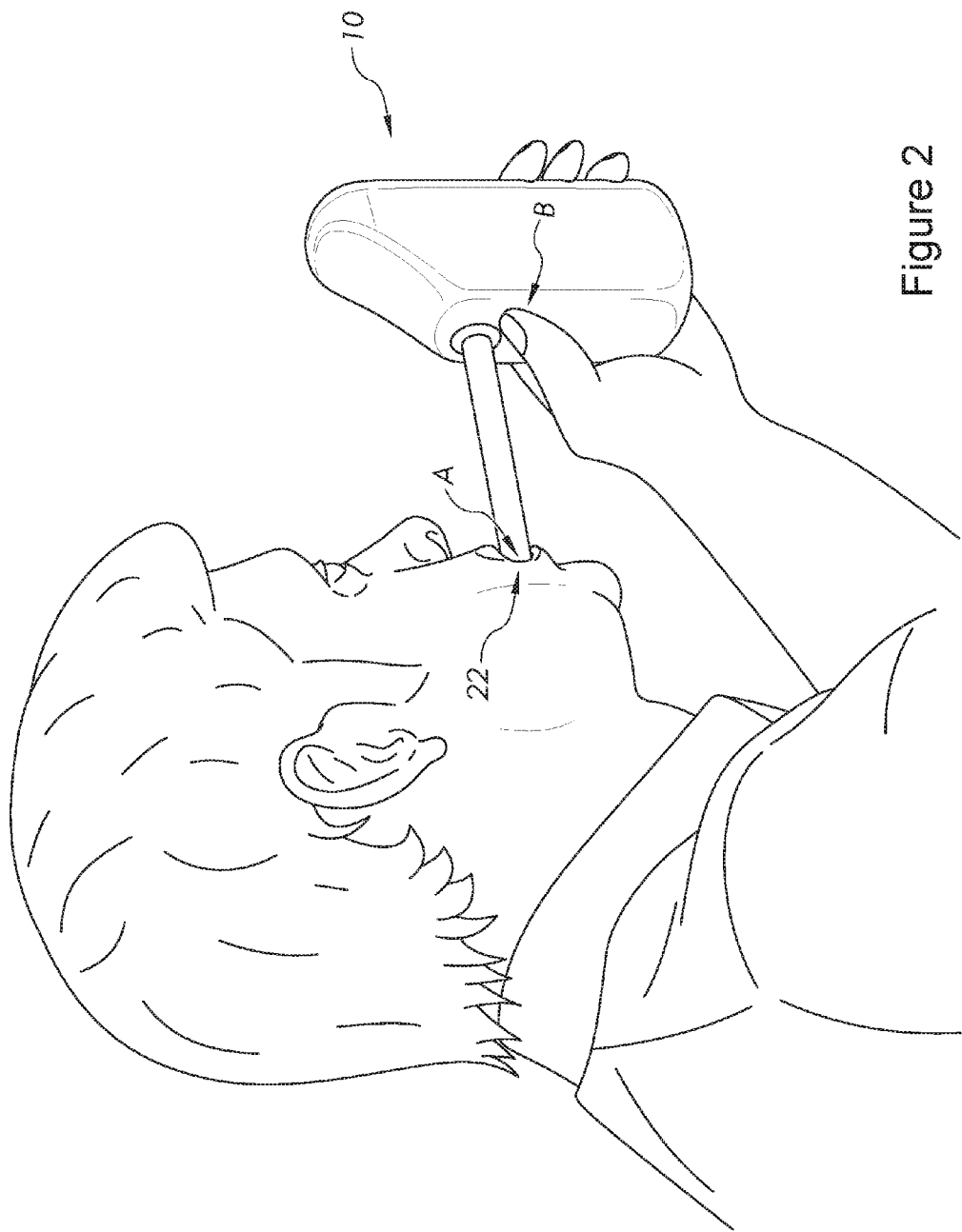
FIG. 2 is a perspective view illustrating an exemplary operation of a breath testing and identification device for monitoring sobriety, according to an embodiment of the invention.

Referring to FIG. 2, an exemplary operation of the substance testing device 10 is shown. The substance testing device 10 may be a hand held substance testing device operable to test for the presence of alcohol or other substance in the breath of the user. The testing device 10 may also operate to test the quantity of alcohol or other substance in the breath of the user. One or more components of the substance testing device 10 can be found in the embodiments described in the incorporated references mentioned herein. For example, the substance testing device 10 may include a breath testing sensor, a printed circuit board (PCB) assembly, a transceiver unit, a GPS module, a camera, and so on.

A shown, when the user operates the substance testing device 10, the user places his or her mouth over the mouthpiece 22 and area A, so that area A is in contact with the user's mouth. The user holds the substance testing device 10 so that his or her fingerprint (e.g., thumb's fingerprint as shown) will be on the UID 24 and in contact with area B. The user blows into the substance testing device 10 while holding the substance testing device 10.

Figure 3:
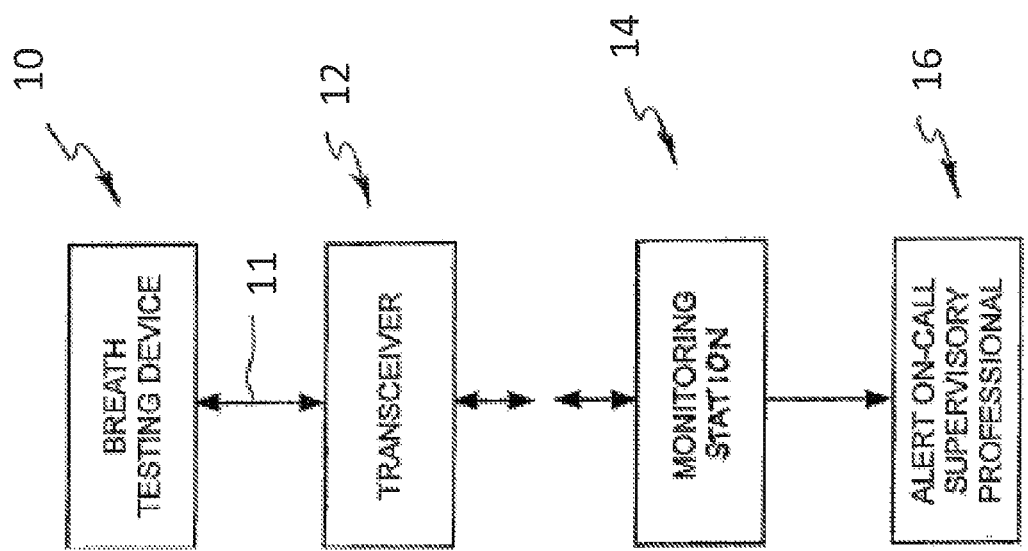
FIG. 3 is a schematic diagram illustrating the method and system for monitoring sobriety, according an embodiment of the invention.

Referring to FIG. 3, in an exemplary embodiment, a substance testing device 10, a transceiver unit 12, a receiving station 14, and a supervisory monitor 16 may be provided for testing and positively identifying a user. The transceiver unit 12 may be configured to transmit a content signal 11 to the receiving station 14. The content signal 11 is generated by the substance testing device 10 and includes at least substance content data. For example, the testing device 10 may be a breathalyzer type testing device operable to analyze the alcohol content of the breath of a user and generate an alcohol content signal indicative of the alcohol content of the user's breath.

The substance content signal 11 may also include a user identification data, for example, fingerprint data. Alternatively, the user identification data may be transmitted to the receiving station 14 separately from the content signal 11.

In some embodiments, the content signal 11 is generated by the substance testing device 10 only if the substance testing device 10 determines that the finger currently on the fingerprint reader is "connected" to the mouth currently on the mouthpiece, and the fingerprint can be positively connected to the breath used for the test as described herein.

In at least one embodiment, the content signal 11 includes a digitized report which may be accessible by a supervisory monitor 16. All transmission described herein may occur over a wireless, wired, cellular, or any other type of network now known or hereafter developed. In at least one embodiment, the transceiver unit 12 is internal to the substance testing device 10 and is a hardware component thereof.

The receiving station 14 may be configured to receive the content signal 11. The receiving station 14 may be configured to inform the supervisory monitor 16 if the content signal 11 is not received from the transceiver at a predetermined time, or if the content signal 11 indicates that the substance content levels exceed a predetermined threshold. For example, the typical legal limit of blood alcohol content (BAC) is 0.08%. Thus, receiving station may inform the supervisory monitor 16 if the content signal indicates the user's BAC is greater than 0.08%. Importantly, the predetermined threshold may be set at a higher or lower level as may be desired. Additionally, the receiving station 14 may be configured to convey the content signal 11, or a report based thereon, directly to the supervisory monitor 16 so that the supervisory monitor 16 is made aware of the substance content data. Thus, for example, the receiving station may inform the supervisory monitor 16 (who may be, for example, a parent or guardian) that the user (who may be, for example, a teenage child of the parent or guardian) has a BAC of 0.03%.

In some embodiments, the receiving station 14 may include any location, device or system where the content signal 11 is received, including, for example: a monitoring station, a cellular/smart phone, an email account, a website, a network database, and a memory device. Additionally, the supervisory monitor 16 may comprise a parent, guardian, family member, friend, parole officer, court appointed supervisor, sobriety coach, sober buddy, sober companion, police department, or other supervisory care person, group, or authority.

Preferably, the entire test and fingerprint reading and user identification process should take less than 60 seconds. The receiving station 14, for example, a monitoring station, website or server, can automatically evaluate the content signal 11 and maintain a history of the test time, result and the user identification data for each test. The receiving station 14 can also include a database and software for analysis of user identification data to confirm or reject the test results, and to determine whether corrective action is required. As explained herein, identification of the user in association with the content signal 11 may be aided by fingerprint recognition. Other recognition techniques now known or developed hereafter, for example, facial recognition, voice recognition, DNA recognition, and iris recognition may also be considered. Additionally, a supervisor may compare the received user identification data with a stored user identification reference in order to positively identify the user. The monitoring station can also provide a variety of reports of the user's testing history or individual test results to allow comprehensive and detailed analysis of the user's testing history, which can be accessed via the Internet as desired. The generated reports may be official Department of Transportation Evidential Breath Testing (EBT) reports, or may be of any other custom or preset format. In some embodiments, still frame photographs or movies used in identification of the user may also be included in the reports.

It will be appreciated that user identification may occur independent of the receiving station 14. For example, a user identification module of the substance testing device 10 may include a memory that may store a reference user identification data for comparison with the generated user identification data. Upon successful comparison, i.e. the actual user is the intended user, the user identification module may communicate a pass signal which may be added to the content signal 11.

As previously described, the substance testing device 10 may include a breathalyzer type device, which includes a mouthpiece 22 configured to be placed at or in a user's mouth during breath testing, and a fingerprint reader device 24. The mouthpiece 22 may be mounted to an end of an extension portion which is in turn connected to a breath analysis and processing portion of the breath testing device 10. The fingerprint reader device 24 may be suitably configured where the user places his thumb during breath testing, and may be configured to read the user's fingerprint in synchronization with the testing of the user's breath, to provide identification information for later use in positive identification of the user with the test results. After the fingerprints have been used to positively identified the user, the testing device 10 will take a resistance measurement between the fingerprint reader 24 and the mouthpiece 22. If the resistance falls within a specified range, the testing device 10 will know that the finger currently on the fingerprint reader 24 is "connected" to the mouth currently on the mouthpiece 22, and the fingerprint can be positively connected to the breath used for the test. For example, if a test is initiated and the resistance value between the mouthpiece 22 and the fingerprint reader 24 is equal to or greater than 4 mega-Ohms, it can be concluded that the mouth and finger do not belong to the same person. If the resistance value between the mouthpiece and the fingerprint reader is less than 4 mega-Ohms it can be concluded that the mouth and finger belong to the same person.

In some embodiments, the mouthpiece 22 may be removable.

The substance testing device 10 may include a status LED, for example, for indicating when the device is ready for use and when the device has completed breath testing and identification.

In some embodiments, the breath testing sensor (not shown) of the testing device 10 includes a sensor capable of detecting the presence of at least one controlled substance or narcotic. The sensor may utilize, for example, a chromatography sensors, mass spectroscopy sensors, fiber optic fluorescent sensors, or surface acoustic wave sensors to detect the presence of controlled substances or narcotics and their derivatives, such as, for example: methamphetamines, amphetamines, barbituates, tetrahydrocannabinol or other cannibanoids, benzoylmethylecgonine, diacetylmorphine or other opiates/opioids, lysergic acid diethylamide, psilocin, phencyclidine and the like, in a user's breath.

The PCB assembly is configured to receive the substance content data and generate a breath test signal 11 therefrom. The PCB assembly is also configured to receive user identification data generated by the fingerprint reader 24 and to generate the breath test signal 11 from the user identification data (which may be compressed) and the substance content data. In some embodiments, the PCB is configured to operate a compression process to compress the user identification data.

Additionally, the substance testing device 10 may utilize software algorithms analyzing pressure and temperature sensor data to ensure that the breath being analyzed is that of a person. Accordingly, the substance testing device 10 may comprise one or more pressure gauges (not shown) and/or temperature sensors (not shown) at various points thereon.

In some embodiments, the substance testing device 10 may be connected to a mobile wireless or cellular transmitter or transceiver device, which may be connected to the substance testing device 10 either directly, such as by an electrical connection, or wirelessly, to receive the breath test signal 11 including breath test data, fingerprint data, photograph, movie, or other user identification data, as well as any GPS location data.

In some embodiments, the substance testing device 10 can also be usable in combination with an iPad™, iPhone™, or other wireless or cellular device, or any other computing device, for example, which can serve as a wireless or cellular transmitter or transceiver device, as discussed herein.

In some embodiments, the content signal 11 including at least one of: content data, user identification data, and location data, can be sent directly from one mobile wireless or cellular transmitter or transceiver device to another mobile wireless or cellular transmitter or transceiver device, without storing one or more of the content data, user identification data, or location data.

The wireless or cellular receiver monitoring station 16 can be configured to receive the content signal comprising at least one of: content data, user identification data, and location data, and to indicate an alarm condition or alert a supervisory monitor either directly or via a network.

In some embodiments, the substance testing device 10 may also be included in or connected to a vehicle ignition interlock signal generating system. The output of the substance testing device 10 may be provided to enable/disable a vehicle ignition lock based on the data received in accordance with the algorithms described above. In addition, an on-call supervisory person may be alerted, and a receiving station 16 may also receive the enable/disable signal as well as the content signal 11 described above.

Figure 4:
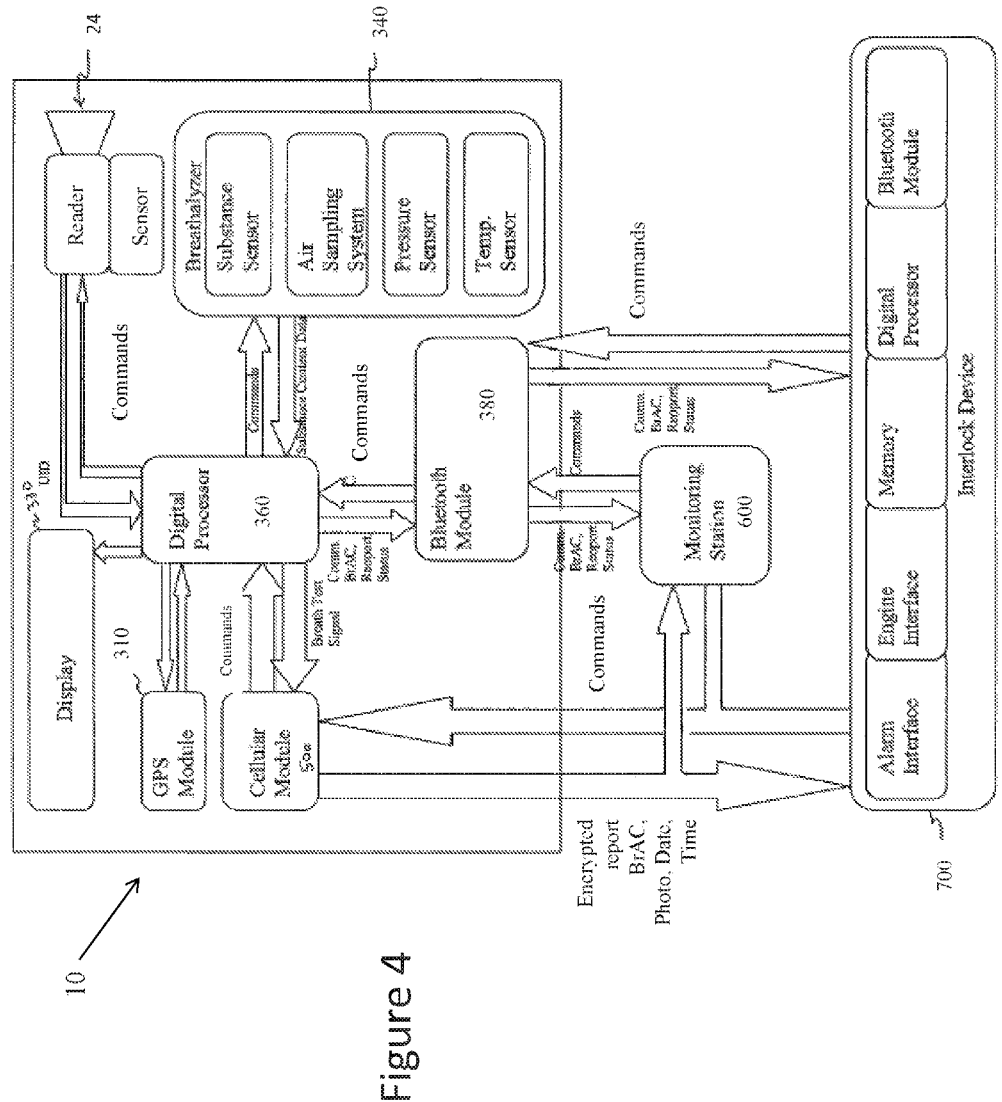
FIG. 4 is a schematic diagram illustrating another the method and system for monitoring sobriety, according to an embodiment of the invention.

Referring to FIG. 4, in an exemplary embodiment, a schematic of a substance testing device 10 is shown. In the example, the substance testing device 10 is a breath testing device. The testing unit 10 may comprise an internal cell module 500, the testing unit 10 here being a stand-alone unit.

The testing unit 10 may include at least: the user identification module 24, the breath analysis module 340, the control module (CPU) 360, the cellular module 500 and a GPS module 310, and so on.

The cellular module 500 may include a transceiver operable to transmit the breath test data to the monitoring station 600. The GPS module 310 may enable the tracking of the testing unit 10 by the generation of location data. A breath test signal may be generated, at least in part, by the location data.

The testing unit 10 may also include a personal area network (PAN) or Bluetooth (or suitable short-range communication) module 380, enabling the testing unit 10 to be in communication with the monitoring station 600. The module 380, for example a vehicle interlock 700.

Communication between the module 380 and the monitoring station may be secured by data encryption techniques now known or hereafter devised. For example, data may be encrypted by means of a random security PIN. Devices that are compromised may be forced from the monitoring station server and may require re-activation and authentication.

The testing unit 10 may also include a graphical user interface 330 (GUI). The GUI may permit the user to interactively control the breath testing process, calibrate the breath testing unit, schedule breath test times, retrieve past breath test reports, and/or access other information stored in the testing unit 10.

The GUI 330 may be configured to display a reminder at a predetermined time, the reminder reminding the user that a breath testing session is due. Additionally, the testing unit 10 may cause users to receive electronic reminders via SMS, email, or bi-directional communication between the testing unit 10 and a receiving station. Additionally, the testing unit 10 may enable the user to receive breath test requests from the monitoring station 600. Such requests may be remotely or directly transmitted to the testing unit 10. Such requests may also be randomly timed.

The testing unit 10 may also include an audio means, such as a speaker, for generating an audio reminder that a breath testing session is due. The tone and/or duration of the audio alert may indicate the urgency of the required breath testing session. For example, three beeps may indicate a session is required immediately, while one beep may indicate a session will be due shortly. The audio means may also be configured to generate a vibration reminder according to methods known in the art.

It will be appreciated, that while at least one embodiment is herein described through example as testing for alcohol use, such embodiments may be equally applicable to testing for the use of controlled substances or other narcotics, as described herein.

Other exemplary embodiments and processes of the substance testing device are further described in the references mentioned above and are incorporated in entirety by reference herein.

The embodiments described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A handheld device for monitoring the sobriety of a user, the handheld device comprising:
   a mouth piece for receiving a user's mouth;
   a conductive area positioned on said mouthpiece;
   a user identification device positioned on a case of the handheld device; and
   a conductive area positioned on said user identification device, wherein the handheld device is configured to obtain a resistance measurement at the conductive area positioned on said mouthpiece and a resistance measurement at the conductive area positioned on said user identification device.

2. The handheld device of claim 1, wherein the handheld device is further configured to measure a difference between the resistance measurement at the conductive area positioned on said mouthpiece and the resistance measurement at the conductive area positioned on said user identification device, and determine whether the difference falls within a specified range.

3. The handheld device of claim 1, further comprising a wireless transceiver.

4. The handheld device of claim 3, further configured to transmit one or more substance content signals.

5. The handheld device of claim 4, wherein the one or more substance content signals include a user identification.

6. The handheld device of claim 5, wherein the user identification is a fingerprint.

7. A handheld device for monitoring the sobriety of a user, the handheld device comprising:
   a mouth piece for receiving a user's mouth and the user's breath;
   a conductive area positioned on said mouthpiece from which a first resistance is measured during operation;
   a user identification device positioned on a case of the handheld device for receiving the user's fingerprint;
   a conductive area positioned on said user identification device from which a second resistance is measured during operation; and
   a wireless transceiver.

8. The handheld device of claim 7, wherein the handheld device is further configured to measure a difference between the first resistance and the second resistance and determine whether the difference falls within a specified range.

9. The handheld device of claim 7, further configured to transmit one or more substance content signals.

10. The handheld device of claim 9, wherein the handheld device is further configured to measure a difference between the first resistance and the second resistance and to transmit the one or more substance content signals if the difference falls within a specified range.

11. The handheld device of claim 9, wherein the one or more substance content signals include a user identification.

12. The handheld device of claim 11, wherein the user identification is a fingerprint.

13. A handheld device for monitoring the sobriety of a user, the handheld device comprising:
   a camera for taking a digital image of the user;
   a mouth piece for receiving a user's mouth and the user's breath;
   a conductive area positioned on said mouthpiece for obtaining a first resistance measurement;
   a user identification device positioned on a case of the handheld device for receiving the user's fingerprint;
   a conductive area positioned on said user identification device for obtaining a second resistance measurement; and
   a wireless transceiver.

14. The handheld device of claim 13, wherein the handheld device is further configured to calculate a difference between the first resistance measurement and the second resistance measurement and determine whether the difference falls within a specified range.

15. The handheld device of claim 13, further configured to transmit one or more substance content signals.

16. The handheld device of claim 15, wherein the one or more substance content signals include one or more user identifications.

17. The handheld device of claim 16, wherein the one or more user identifications include a fingerprint.

18. The handheld device of claim 16, wherein the one or more user identifications include a digital image.

19. The handheld device of claim 16, wherein the one or more user identifications include one or more of a fingerprint and a digital image.

* * * * *